United States Patent
Parker et al.

(10) Patent No.: US 8,403,940 B2
(45) Date of Patent: Mar. 26, 2013

(54) TOOL TO DISSECT OR COMPRESS AND MEASURE A VERTEBRAL BODY SEGMENT

(75) Inventors: Jared Parker, Denver, CO (US); James Corin, Boulder, CO (US); Alan Burkholder, Denver, CO (US)

(73) Assignee: Lanx, Inc., Broomfield, CO (US)

( * ) Notice: Subject to any disclaimer, the term of this patent is extended or adjusted under 35 U.S.C. 154(b) by 1321 days.

(21) Appl. No.: 12/033,337

(22) Filed: Feb. 19, 2008

(65) Prior Publication Data
US 2008/0200919 A1 Aug. 21, 2008

Related U.S. Application Data

(60) Provisional application No. 60/890,561, filed on Feb. 19, 2007.

(51) Int. Cl.
*A61B 17/58* (2006.01)
(52) U.S. Cl. .......................................... 606/105; 606/60
(58) Field of Classification Search .................... 606/60, 606/86 A, 90, 102, 246–278, 279, 99, 105
See application file for complete search history.

(56) References Cited

U.S. PATENT DOCUMENTS

| 4,335,715 | A | * | 6/1982 | Kirkley | 606/87 |
| 5,891,150 | A | * | 4/1999 | Chan | 606/96 |
| 6,620,168 | B1 | * | 9/2003 | Lombardo et al. | 606/88 |
| 7,004,947 | B2 | * | 2/2006 | Shluzas et al. | 606/105 |
| 7,160,300 | B2 | * | 1/2007 | Jackson | 606/273 |
| 7,794,464 | B2 | * | 9/2010 | Bridwell et al. | 606/86 A |
| 7,951,175 | B2 | * | 5/2011 | Chao et al. | 606/279 |
| 2003/0060826 | A1 | * | 3/2003 | Foley et al. | 606/61 |
| 2004/0138662 | A1 | * | 7/2004 | Landry et al. | 606/61 |
| 2006/0036255 | A1 | * | 2/2006 | Pond et al. | 606/86 |

* cited by examiner

*Primary Examiner* — Kevin T Truong
*Assistant Examiner* — Christopher Beccia
(74) *Attorney, Agent, or Firm* — Holland & Hart LLP (57) ABSTRACT

The present invention provides tools to distract, compress, and measure a vertebral body segment. In one aspect of the invention, a tool includes a handle assembly and a locking mechanism operable between a first condition in which handle portions can translate and pivot relative to one another and a second condition in which the handle portions are fixed translatably. In another aspect of the invention, a tool for distracting and compressing a vertebral body segment includes a measuring device to simultaneously indicate the length of a connecting element for coupling the fasteners. In another aspect of the invention, a measurement device includes indicia defined by a locus of points corresponding to a particular connecting element length. In another aspect of the invention, a method of coupling a first fastener engaged with a first vertebrae to a second fastener engaged with a second vertebrae is provided.

18 Claims, 7 Drawing Sheets

TOOL TO DISSECT OR COMPRESS AND MEASURE A VERTEBRAL BODY SEGMENT

CROSS-REFERENCE TO RELATED APPLICATIONS

This application claims the benefit of U.S. Provisional Application No. 60/890,561, filed Feb. 19, 2007.

FIELD OF THE INVENTION

The technology of the present application relates generally to spinal surgery, and more specifically to tools that distract, compress, and measure a spinal vertebral segment.

BACKGROUND

Currently, in the art, a minimally invasive spinal fusion procedure, for example, is accomplished by threading pedicle screws to pedicles of adjacent vertebrae defining a spinal segment using screw extenders. A distraction device is attached to the screw extenders of a spinal segment the surgeon desires to distract. Distraction force is applied. While the distraction is ongoing, a measurement tool is inserted through the hollow tubes to measure the distance between the pedicles.

In some cases, the surgeon desires to compress the segment. The distraction tool is not usable to compress the segment, but rather a compression tool is used. Similarly, to measure the distance between the pedicles after compression is applied, a measurement tool is inserted through the screw extenders.

In other cases, the distance between pedicles is measured without any compression or distraction force to yield an approximate measurement of the distance between pedicles.

Current compression tools and distraction tools are bulky and inflexible in their positioning and use. They require multiple steps to assembly multiple components to the screw extenders. Likewise, existing measurement tools require multiple steps to assemble multiple components to the screw extenders. Improved tools are needed to distract, compress, and measure a vertebral segment.

SUMMARY

The present invention provides tools to distract, compress, and measure a vertebral body segment.

In one aspect of the invention, a tool for distracting and compressing a vertebral body segment includes a handle assembly and a locking mechanism operable between a first condition in which the first and second handle portions can translate and pivot relative to one another and a second condition in which the first and second handle portions are fixed translatably relative to one another and the first and second handle portions can pivot relative to one another. First and second grips are responsive to movement toward one another to move first and second engagement means closer together, second and third grips are responsive to movement toward one another to move the first and second engagement means further apart.

In another aspect of the invention, a tool for distracting and compressing a vertebral body segment includes a handle assembly selectively operable to move first and second engagement means toward and away from one another. The tool further includes a measuring device to simultaneously indicate the length of a connecting element for coupling the fasteners.

In another aspect of the invention, a tool for determining the length of a connecting element needed to bridge between first and second fasteners mounted to first and second vertebral bodies of a vertebral body segment includes first and second engagement means mounted for translation and pivoting relative to one another. Indicia mounted relative to the first and second engagement means are each defined by a locus of points corresponding to a particular connecting element length and each point corresponds to one of a plurality of relative translated and angular positions of the first and second engagement means for the particular connecting element length such that the indicia and pointer indicate the connecting element length for a plurality of combinations of relative translated and angular positions of the first and second engagement means.

In another aspect of the invention, a method of coupling a first fastener engaged with a first vertebrae to a second fastener engaged with a second vertebrae includes translating and pivoting first and second portions of a tool relative to one another to align the first and second portions with the first and second fasteners; coupling the first portion of the tool to the first fastener; coupling the second portion of the tool to the second fastener; locking the first and second portions to prevent relative translation between them while permitting relative pivoting between them; and pivoting the first and second portions to one of compress and distract the first and second vertebrae relative to one another.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

The technology of the present invention will be described in the context of spinal surgery, but one of ordinary skill in the art will recognize that the technology may be applicable to other medical fields. Moreover, the technology of the present application will be described with reference to certain exemplary embodiments. The word "exemplary" is used herein to mean "serving as an example, instance, or illustration." Any embodiment described herein whether or not specifically identified as "exemplary" is not to be construed as preferred or advantageous over other embodiments.

Figure 1:
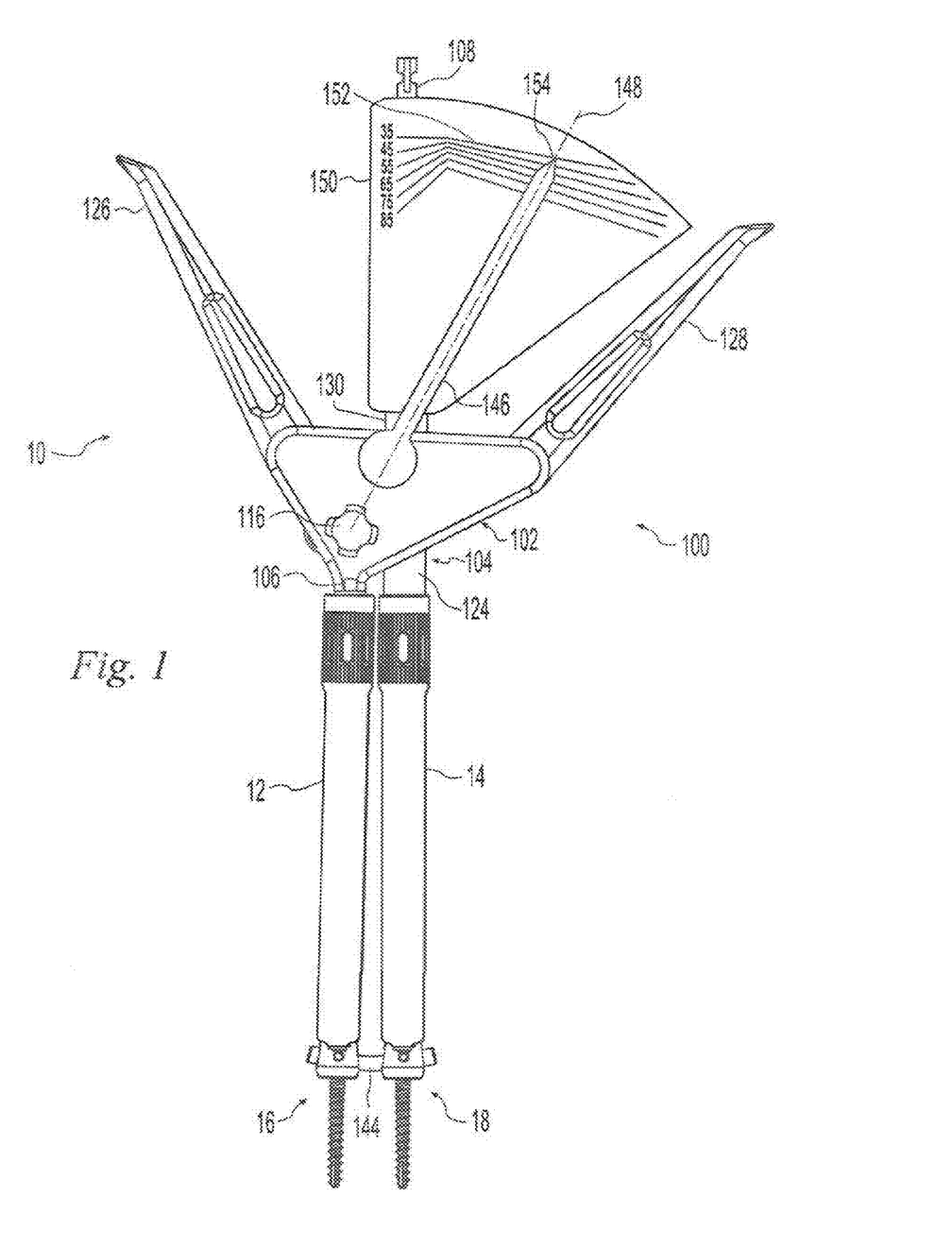
FIG. 1 is a front elevation view of a tool according to the present invention.
Figure 2:
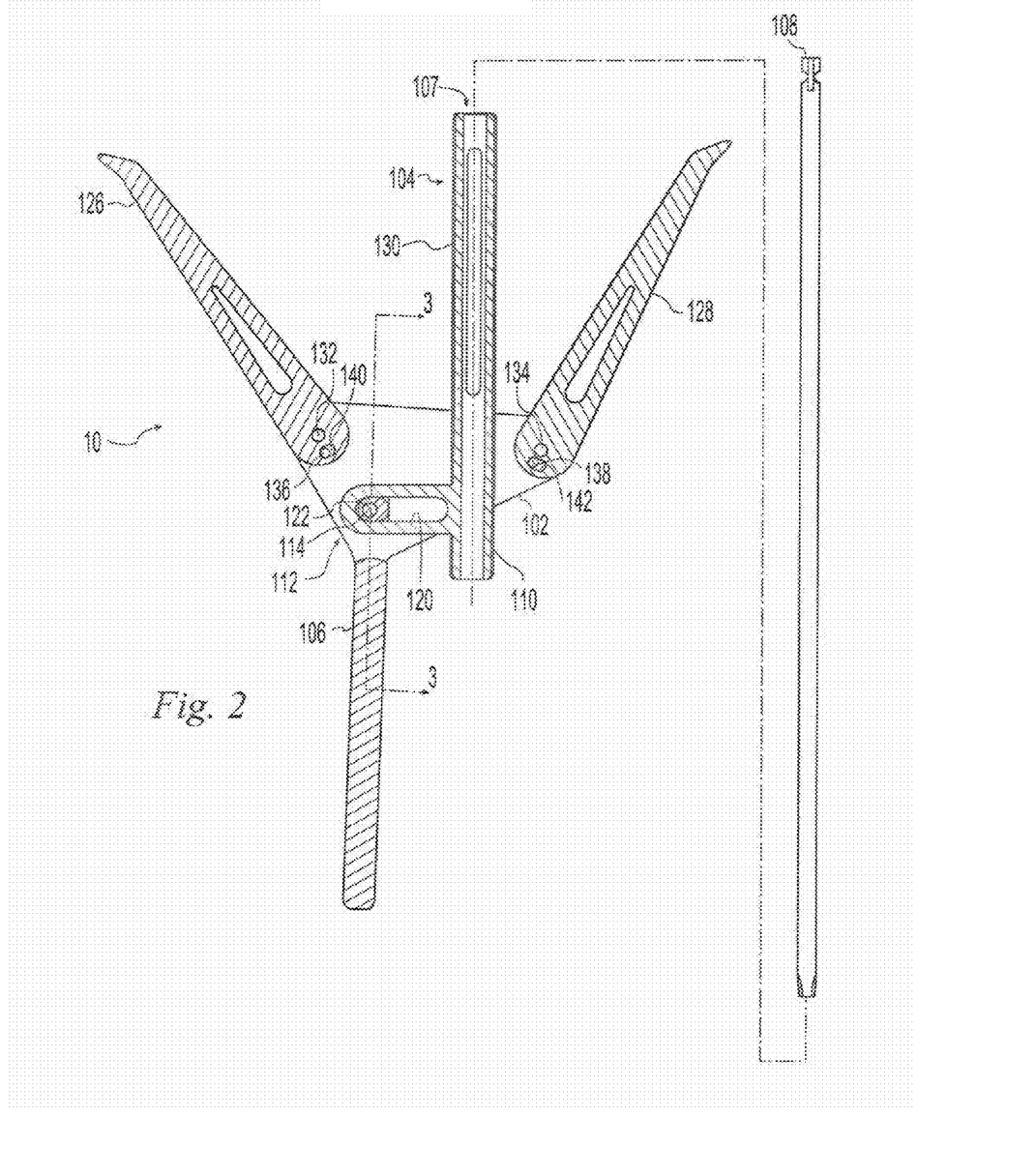
FIG. 2 is a cross sectional view of the tool of FIG. 1.
Figure 3:
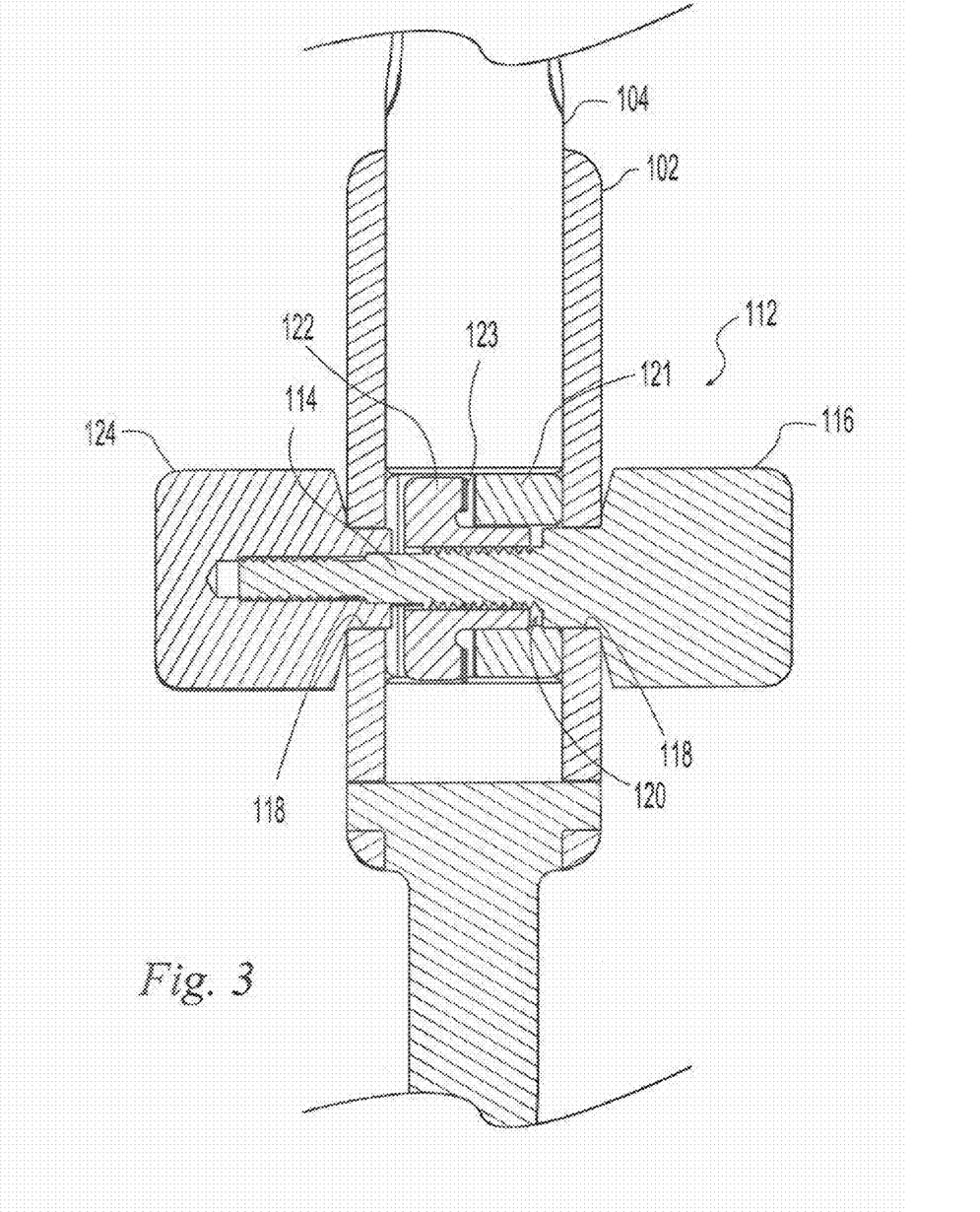
FIG. 3 is a cross sectional view of the tool of FIG. 1.

Referring first to FIG. 1, tool 10 includes a handle assembly 100 and a graduated measuring device 150. The tool 10 is shown coupled to screw extenders 12, 14 that extend respective pedicle screws 16, 18, which would be coupled to vertebral bodies. In the illustrative example, the screw extenders 12, 14 are shown in the form of hollow tubes releasably engaged with the pedicle screws 16, 18. The screw extenders 12, 14 are generally known in the art and will not be further explained herein. FIGS. 2 and 3 show cross sections of the handle assembly 100.

The handle assembly 100 has a first handle portion 102 and a second handle portion 104. The first handle portion 102 has a protrusion 106 that couples to one of the screw extenders 12. The second handle portion 104 has a hollow channel 107 (FIG. 2) to accept a pedicle screw driver 108 or the like. The driver 108 extending through hollow channel 107 and extending through the screw extender 14 couples the second handle portion 104 to the screw extender 14. Alternatively, the second handle portion 104 may couple directly to the screw extension 14 such as by a protrusion 110 extending into the screw extension 14.

As shown in FIGS. 2 and 3, first handle portion 102 and second handle portion 104 are slidably and pivotally coupled together by a releasable locking mechanism 112. The locking mechanism 112 has a threaded axle 114 connected to a first head 116. The axle 114 extends through a bore 118 in the first handle portion 102, through a groove 120 in a tab 121 extending from the second handle portion 104, and threadably engages a stop 122. The axle 114 extends completely through the first handle portion 102 and a second head 124 is mounted on the protruding end. The first and second heads 116, 124 are permanently fixed to the axle 114 such that rotating either of the first and second heads 116, 124 causes axle 114 to rotate and the stop 122 to translate along the axle 114 between a first position in which the stop 122 is engaged with the tab 121 to prevent the second handle portion 104 from translating relative to the first handle portion 102 and a second position in which the stop 122 is disengaged from the tab 121 to allow the second handle portion 104 to translate relative to the first handle portion 102. The stop 122 may engage the tab 121 frictionally and/or positively. For example, optional teeth 123 may be formed on the abutting surfaces of the stop 122 and tab 121 so that they positively engage.

When the stop 122 is disengaged, the first handle portion 102 and second handle portion 104 can move laterally with respect to one another as the axle 114 moves along the groove 120 and they can move pivotally with respect to each other about the axle 114 as a pivot point. Thus when the stop 122 is disengaged, the spacing of the handle portions 102, 104 can be adjusted to fit the screw extenders 12, 14 which will be spaced and angled differently depending on the placement of the pedicle screws 16, 18, patient anatomy, and other variations in each surgical case. When the stop 122 is engaged, the first handle portion 102 and second handle portion 104 are fixed laterally relative to one another but can still pivot with respect to each other about the axle 114 with the application of torque.

The tool 10 has three grips. A distract grip 126 and a compress grip 128 mounted to the first handle portion 102 and a central grip 130 defined by the second handle portion 104. The central grip 130 is referred to as central because it resides between distract grip 126 and compress grip 128 and not because of general orientation (although it could be centered between the other grips). In the illustrative embodiment (FIG. 2), the distract grip 126 and compress grip 128 are mounted to the first handle portion 102 in pivoting relationship about pivot pins 132, 134 and are constrained to a limited pivot range by stop pins 136, 138 engaged in slots 140, 142. The pivoting relationship of the grips 126, 128, permits a grip that is not being used (e.g. distract grip 126 in FIG. 2) to pivot away from the central grip 130 to provide increased clearance for a user's fingers. Likewise, the pivoting relationship permits a grip that is being used (e.g. compress grip 128 in FIG. 2) to pivot toward the central grip 130 to allow easy gripping of both the central grip 130 and the other grip being used.

To distract a vertebral segment, a surgeon would grasp the distract grip 126 and the central grip 130. The surgeon would apply compressive force to move the distract grip 126 relatively towards the central grip 130. The compressive force causes the first and second handle portions 102, 104 to pivot relative to one another about the axle 114 and the screw extenders 12, 14 to move apart to distract the vertebral segment. To compress the vertebral segment, a surgeon would grasp compress grip 128 and central grip 130. The surgeon would apply compressive force to move the compress grip 128 relatively towards central grip 130. The compressive force causes the first and second handle portions 102, 104 to pivot relative to one another about the axle 114 and the screw extenders 12, 14 to move toward one another to compress the vertebral segment.

To complete, for example, conventional spinal fusion, the surgeon would next measure a distance between the pedicle screws 16, 18. The distance corresponds to the length of a rod 144 (FIG. 1) needed to bridge between the pedicle screws 16, 18 to fix them relative to one another and in a conventional manner to facilitate fusion. To facilitate measuring the distance a pointer 146 is mounted to the first handle portion 102 using a connection that may be for example, a press fit connection, friction fitting, snap lock connection, threaded connection or the like. In the illustrative example, the longitudinal axis 148 of the pointer 146 is aligned with the axle 114. A graduated measuring device 150 having a plurality of indicia 152 corresponding to various pedicle screw spacings is mounted on the central grip 130. The graduated measuring device 150 fits the central grip 130 such that when it is placed on the central grip 130, the tip 154 of the pointer resides about one of the plurality of indicia 152 indicating a distance corresponding to the length of rod 144 required to bridge between the pedicle screws 16, 18. The indicia 152 are each defined by a locus of points in the form of a line or curve corresponding to a particular rod length. As the angle between the screw extenders increases, the graduated-measuring device 150 will tip relative to the pointer 146 and the pointer 146 will indicate increasing rod length. Likewise, as the first and second handle portions 102, 104 are translated away from one another by disengaging the locking mechanism 112 and sliding the handle portions 102, 104 relatively outwardly, the graduated measuring device 150 will slide to the right relative to the pointer 146 and the pointer will indicate increasing rod length due to the angled orientation of the indicia 152. Thus, each indicia is defined by a locus of points corresponding to a particular rod length. Each point corresponds to one of a plurality of relative lateral and angular positions of the first and second handle portions 102, 104 for the particular rod length such that the graduated measuring device 150 and pointer 146 will indicate the proper rod length for a plurality of combination of lateral spacing and angular orientation of the first and second handle portions 102, 104. The indicia may be a series of discrete points. The indicia may alternatively be in the form of continuous marks. The indicia may be determined empirically by measuring and/or modeling the position of the parts for different discrete arrangements or they be calculated as a mathematical function. This arrangement of adjustable first and second handle portions 102, 104 and a measurement device having individual indicia defined by a locus of points corresponding to a plurality of combinations of spacing and angular orientation of the handles portions allows the instrument to be adjusted to fit a particular patient anatomy and screw placement while still indicating a correct rod length. In the present invention, the screw extenders 12, 14 can be rigidly coupled to the pedicle screws 16, 18 for positive control of the screws 16, 18 and the screw head orientation since the tool 10 can be adjusted to fit the angle of the screw extenders 12, 14. This is an improvement over the prior art in which the measurement device is a simple angle indicator and the screws and screw extenders have to be adjusted to fit the inflexible configuration of the prior art measurement device.

The tool 10 may be removed to facilitate placing a rod to bridge the pedicle screws 16, 18. A set screw is tightened to couple the rod to one of the pedicle screws 16 and then the tool is again engaged with the screw extenders 12, 14. With the vertebral segment compressed or distracted to the desired position, the driver 108 is rotated to tighten a set screw to couple the rod to the other pedicle screw 18 and fix the spacing of the pedicle screws and thus the vertebral segment.

FIGS. 4-7 illustrate a measurement device 200 functionally similar to that of FIGS. 1-3 but able to be used independently of the first and second handle portions. This stand alone measurement device 200 includes a body 204 with a first screw extension engagement portion in the form of a fixed post 206 mounted to the body 204 and a slot 208 in the body 204. The pointer 210 is fixed to a bushing 212 that rides in the slot in translating and pivoting arrangement to allow the pointer 210 to translate and pivot relative to the body 204. The bushing 212 receives a second screw extension engagement portion in the form of a mobile post 214 mounted to the bushing 212 for axial sliding within the bushing 212. As the mobile post 214 translates and pivots relative to the fixed post 206, the bushing 212 and pointer 210 move with it. The body includes indicia 216 each of which is defined by a locus of points corresponding to a particular rod length. Each point corresponds to one of a plurality of relative lateral and angular positions of the fixed and mobile posts 206, 214 for a particular rod length. The measurement device 200 may be coupled to the screw extenders 12, 14 regardless of a particular patient anatomy and screw placement and still indicate a correct rod length. The sliding of the mobile post 214 axially relative to the bushing 212 aids assembly to the screw extenders 12, 14 by allowing the mobile post 214 to be withdrawn upwardly (FIG. 6) so that the fixed post 206 may first be coupled to a screw extender 12 and the mobile post 214 then extended downwardly (FIG. 4) to couple to the other screw extender 14.

Figure 4:
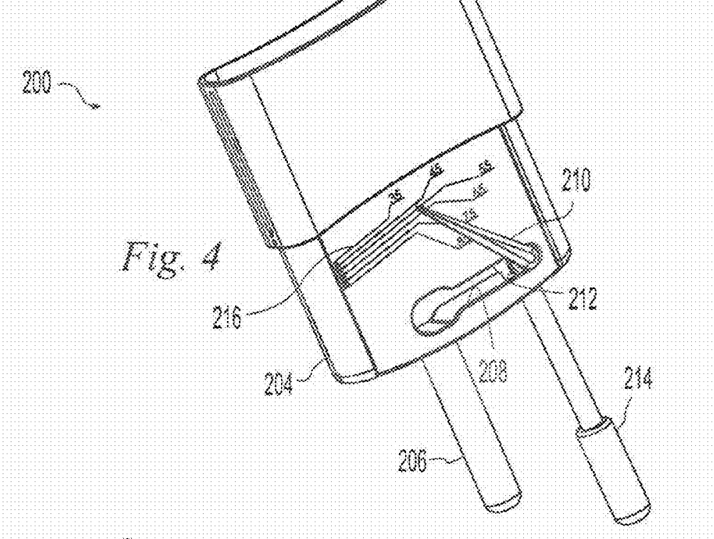
FIG. 4 is a perspective view of a tool according to the present invention.
Figure 5:
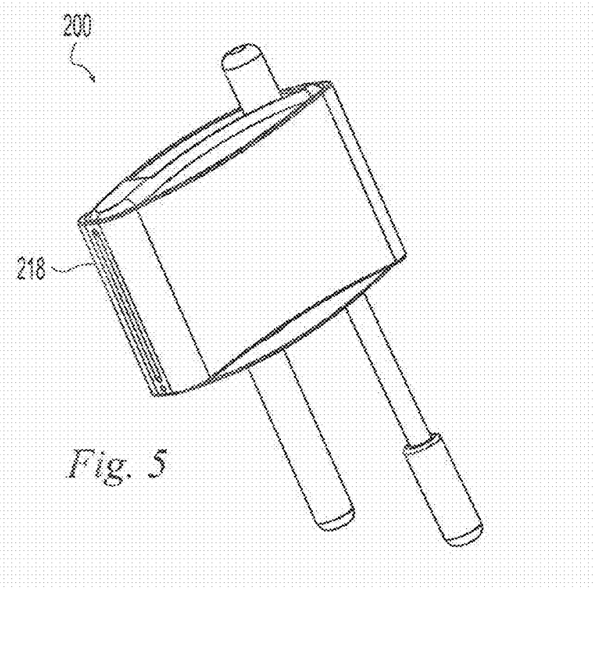
FIG. 5 is a perspective view of the tool of FIG. 4.
Figure 6:
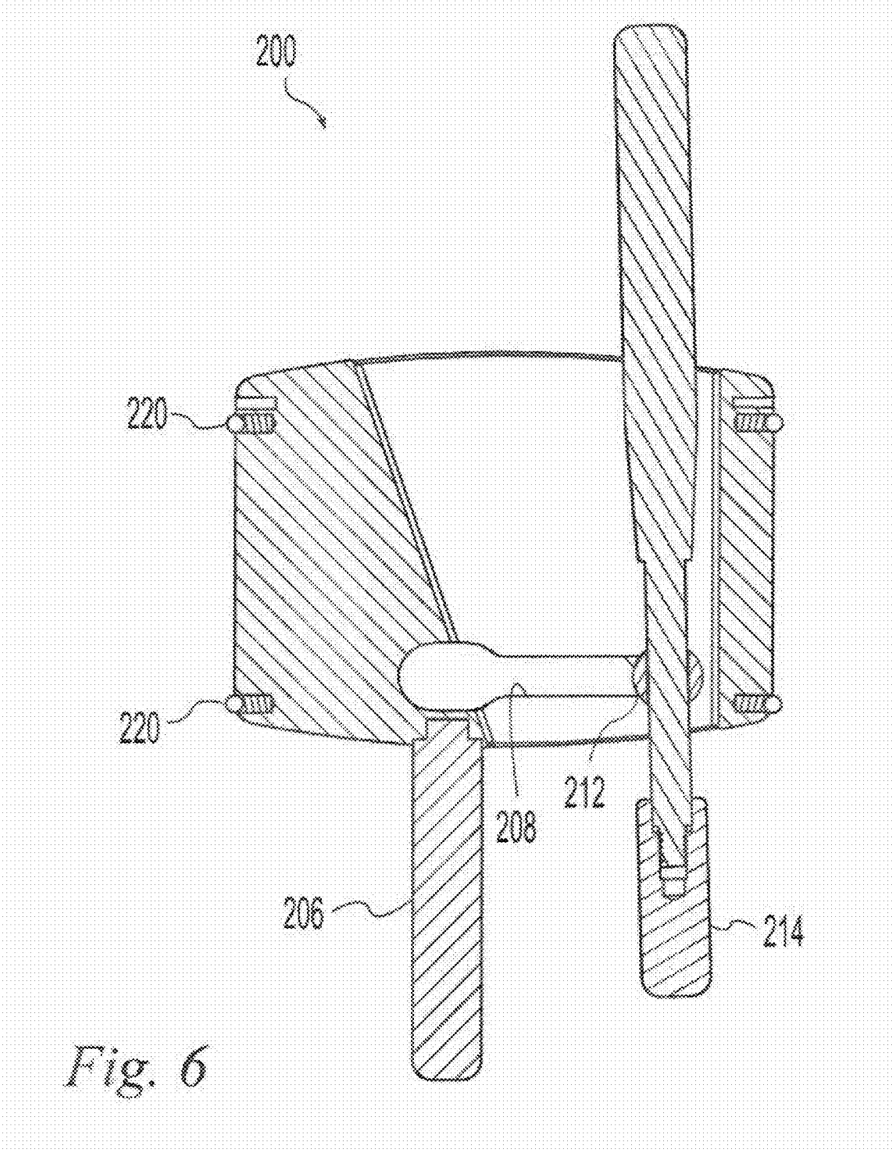
FIG. 6 is a cross sectional view of the tool of FIG. 4.

FIGS. 4 and 5 illustrate a cover 218 slidably engaged with the body 204 and movable from a first position (FIG. 4) in which the pointer 210 and indicia 216 are uncovered and a second position (FIG. 5) in which the pointer 210 and indicia 216 are covered and protected from impacts and abrasion that might occur during cleaning and storage. In the illustrative example, the body 204 includes ball plungers 220 that engage the cover and selectively retain it in the first and second positions. The cover is omitted from FIGS. 6 and 7 for simplicity and clarity in illustrating the body 204.

Figure 7:
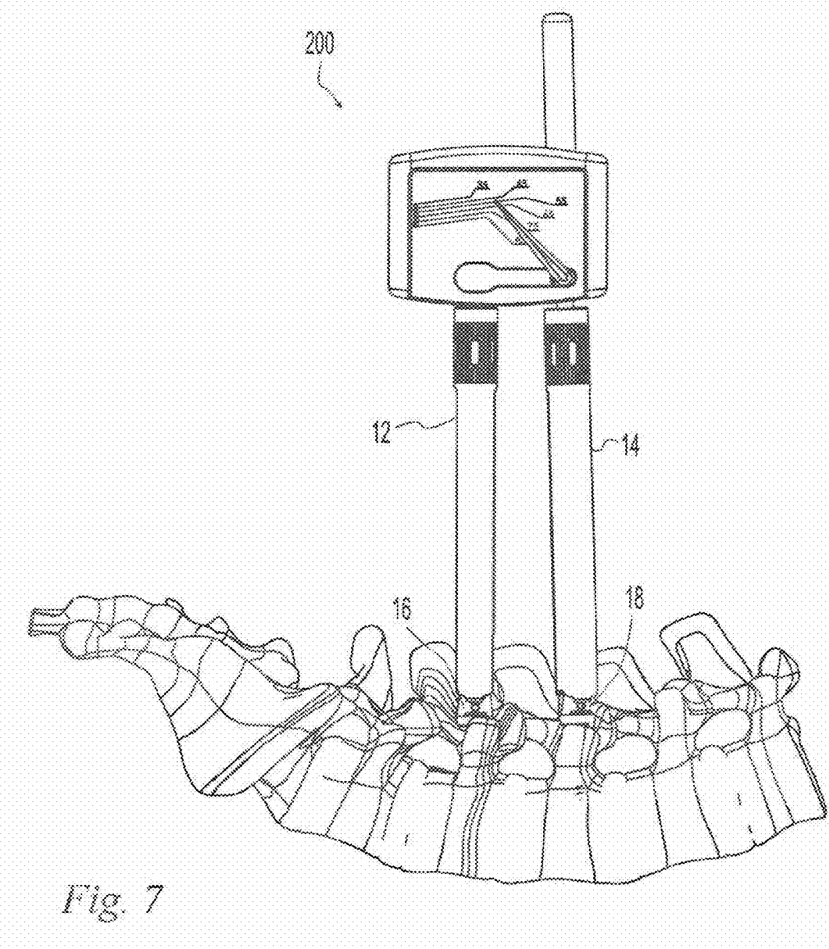
FIG. 7 is a front elevation view of the tool of FIG. 4 in use to measure for a rod between two pedicle screws in a spinal segment.

FIG. 7 illustrates the measurement device 200 in use to determine the rod length required to bridge two pedicle screws 16, 18.

Figure 8:
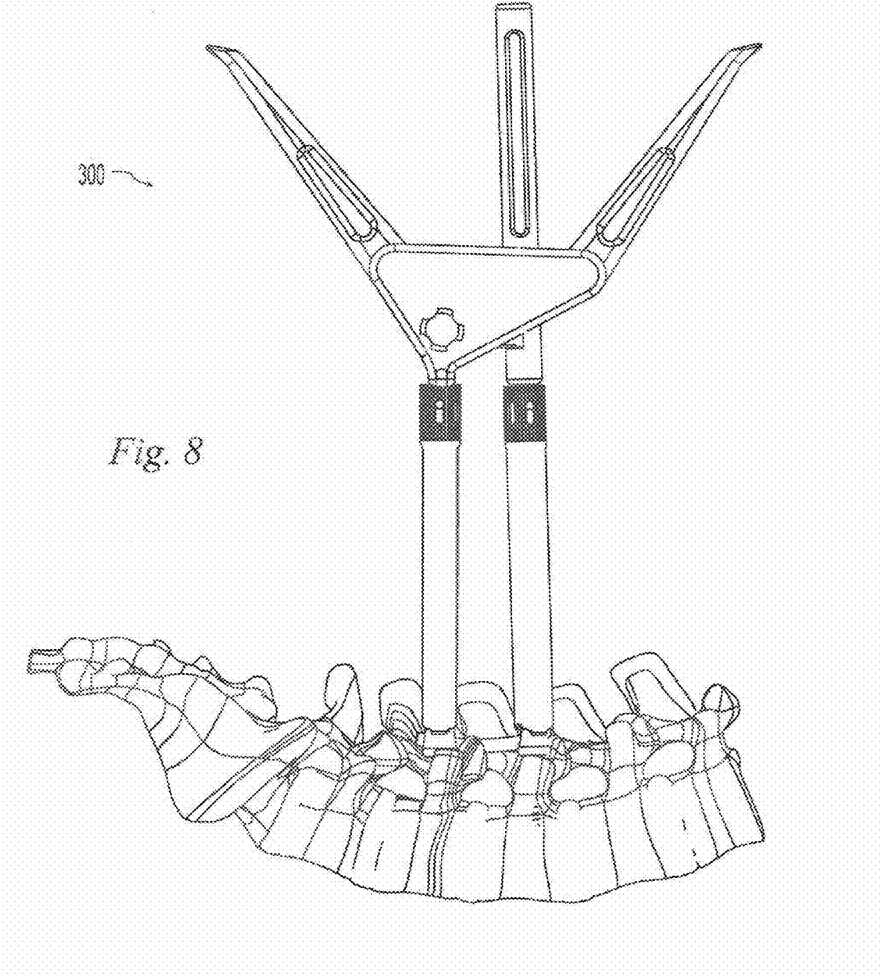
FIG. 8 is a front elevation view of a tool according to the present invention in use dot compress a spinal segment.

FIG. 8 illustrates a tool 300 similar to that of FIG. 1, but without the pointer 146 and graduated measuring device 150, in use to compress or distract a spinal segment. It is contemplated and within the scope of the present invention that a tool can combine compression, distraction, and measurement as shown in the embodiment of FIG. 1 or that these functions can be separated into a measurement device as shown in FIG. 4 and a tool for compression and distraction as shown in FIG. 8. Furthermore, in the embodiment of FIG. 1, the pointer 146 and graduated measuring device 150 may be permanently assembled to the handle portions 102, 104 or may be modular and selectively mountable to the first and second handle portions 102, 104.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A single tool that allows for both distracting and compressing a vertebral body segment including first and second vertebral bodies to be joined together with a first fastener mounted to the first vertebral body, a second fastener mounted to the second vertebral body, and a connecting element coupled to the fasteners, the single tool comprising:
a handle assembly, the handle assembly including a first handle portion and a second handle portion mounted for translation and pivoting relative to the first handle portion;
a releasable locking mechanism operable between a first condition in which the first and second handle portions can translate and pivot relative to one another and a second condition in which the first and second handle portions are fixed translatably relative to one another and the first and second handle portions can pivot relative to one another;
the handle assembly comprising:
a first grip operably associated with the first handle portion;
a second grip operably associated with the first handle portion;
a third grip operably associated with the second handle portion;
first engagement means associated with the first handle portion; and
second engagement means associated with the second handle portion;
the first and second grips being responsive to movement toward one another to move the first and second engagement means closer together; and
the second and third grips being responsive to movement toward one another to move the first and second engagement means further apart.

2. The single tool of claim 1 further comprising a fastener extension engaged with the first fastener, one of the first, and second engagement means comprising a protrusion engageable with the fastener extension.

3. The single tool of claim 1 further comprising a fastener extension engaged with the first fastener and a screw driver, one of the first and second engagement means comprising a hollow tube, the screw driver being receivable through the hollow tube and the fastener extension to couple the hollow tube to the fastener extension.

4. The single tool of claim 1 wherein the locking mechanism comprises an axle and a stop threadably engaged with the axle, the stop being responsive to rotation of the axle to move between a first position in which the stop prevents relative translation of the first and second handle portions and a second position in which relative translation of the first and second handle portions is permitted.

5. The single tool of claim 1 wherein the third grip is positioned between the first and second grips.

6. The single tool of claim 1 wherein at least one of the first and second grips is mounted to the first handle portion in pivoting relationship.

7. The single tool of claim 1 further comprising a measuring device mounted between the first and second handle portions to indicate the length of the connecting element for coupling to the fasteners.

8. The single tool of claim 7 wherein the measuring device, comprises indicia mounted to one of the first and second handle portions and a pointer mounted to the other of the first and second handle portions, the pointer residing near one of the indicia to indicate the length of the connecting element.

9. The single tool of claim 8 wherein the indicia are each defined by a locus of points corresponding to a particular connecting element length and wherein each point corresponds to one of a plurality of relative translated and angular positions of the first and second handle portions for the particular connecting element length such that the indicia and pointer indicate the connecting element length for a plurality of combinations of relative translated, and angular positions of the first and second handle portions.

10. The single tool of claim 9 wherein the indicia comprise discrete points.

11. The single tool of claim 9 wherein the indicia comprise continuous marks.

12. The single tool of claim 8 further comprising a cover mounted to the measuring device and being moveable between a first position in which the indicia and pointer are uncovered and a second position in which the indicia and pointer are covered.

13. A single tool that allows for both distracting and compressing a vertebral body segment including first and second vertebral bodies to be joined together with a first fastener mounted to the first vertebral body, a second fastener mounted to the second vertebral body, and a connecting element coupled to the fasteners, the single tool comprising:
   a handle assembly, the handle assembly including a first handle, portion and a second handle portion mounted for movement relative to the first handle portion;
   the handle assembly comprising:
   first engagement means associated with the first handle portion; and
   second engagement means associated with the second handle portion;
   the handle assembly being selectively operable to move the first and second engagement means toward and away from one another; and
   a measuring device mounted between the first and second handle portions to simultaneously indicate the length of the connecting element for coupling to the fasteners.

14. The single tool of claim 13 wherein the measuring device includes indicia, each of the indicia being defined by a locus of points corresponding to a particular connecting element length and wherein each point corresponds to one of a plurality of relative positions of the first and second handle portions for the particular connecting element length such that the indicia and pointer indicate the connecting element length for a plurality of combinations of relative positions of the first and second handle portions.

15. The single tool of claim 13 further comprising a cover mounted to the measuring device and being moveable between a first position in which the indicia and pointer are uncovered and a second position in which the indicia and pointer are covered.

16. A tool for determining the length of connecting element needed to bridge between first and second fasteners mounted to first and second vertebral bodies of a vertebral body segment of a spine, the tool comprising
   first engagement means;
   second engagement means mounted for translation and pivoting relative to the first engagement means; and
   indicia mounted relative to the first and second engagement means; each of the indicia being defined by a locus of points corresponding to a particular connecting element length and wherein each point corresponds to one of a plurality of relative translated and angular positions of the first and second engagement means for the particular connecting element length such that the indicia and pointer indicate the connecting element length for a plurality of combinations of relative translated and angular positions of the first and second engagement means.

17. The tool of claim 16 further comprising a body with a slot and a bushing mounted in the slot for translation along the slot and pivoting within the slot, a pointer fixed to the bushing and extending near the indicia, wherein the first engagement means comprises a first post fixed to the body and the second engagement means comprises a second post mounted to the bushing for pivoting and translation with the bushing along the slot relative to the fixed post.

18. The tool of claim 16 further comprising a cover mounted relative to the indicia and being moveable between a first position in which the indicia are uncovered and a second position in which the indicia are covered.

* * * * *